US010755815B2

(12) United States Patent
Graf

(10) Patent No.: US 10,755,815 B2
(45) Date of Patent: Aug. 25, 2020

(54) METHOD FOR OPERATING A MEDICAL SYSTEM, COMPUTER PROGRAM PRODUCT, MEDICAL SYSTEM, AND CONTROL DEVICE

(71) Applicant: Roche Diabetes Care, Inc., Indianapolis, IN (US)

(72) Inventor: Markus Graf, Worms (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 196 days.

(21) Appl. No.: 16/071,112

(22) PCT Filed: Jan. 25, 2017

(86) PCT No.: PCT/EP2017/051466
§ 371 (c)(1),
(2) Date: Jul. 19, 2018

(87) PCT Pub. No.: WO2017/129579
PCT Pub. Date: Aug. 3, 2017

(65) Prior Publication Data
US 2020/0176109 A1    Jun. 4, 2020

(30) Foreign Application Priority Data

Jan. 27, 2016 (EP) ..................... 16153000

(51) Int. Cl.
*G16H 40/00* (2018.01)
*G16H 40/67* (2018.01)
(Continued)

(52) U.S. Cl.
CPC ............... *G16H 40/67* (2018.01); *A61B 5/01* (2013.01); *A61B 5/024* (2013.01);
(Continued)

(58) Field of Classification Search
CPC .... G16H 40/67; G16H 10/60; G08B 21/0453; A61B 5/01; A61B 5/024; A61B 5/14532; A61B 5/7405; A61B 5/742
(Continued)

(56) References Cited

U.S. PATENT DOCUMENTS

2015/0116112 A1    4/2015  Flinsenberg et al.

FOREIGN PATENT DOCUMENTS

| EP | 2845135 | 3/2015 |
| WO | WO 2013/184721 | 11/2013 |
| WO | WO 2015/066051 | 5/2015 |

OTHER PUBLICATIONS

Ren-Guey Lee et al: "A Mobile Care System With Alert Mechanism", IEEE Transactions on Information Technology in Biomedicine, IEEE Service Center, Los Alamitos, CA, US, vol. 11, No. 5, Sep. 1, 2007 (Sep. 1, 2007), pp. 507-517.

*Primary Examiner* — Ojiako K Nwugo
(74) *Attorney, Agent, or Firm* — Woodard, Emhardt, Henry, Reeves & Wagner LLP

(57) ABSTRACT

The present disclosure relates to a method for operating a medical system, comprising: providing a first threshold value for the physiological parameter in the control device, the first threshold value being assigned to a first receiving device configured to notify a user of the first receiving device in response to receiving signaling data from the control device; providing a second threshold value for the physiological parameter in the control device, the second threshold value being different from the first threshold value and assigned to a second receiving device which is different from the first receiving device and configured to notify a user of the second receiving device in response to receiving the signaling data from the control device; receiving a stream of monitoring data indicating a physiological parameter continuously monitored by the sensor device in the
(Continued)

Figure 1:
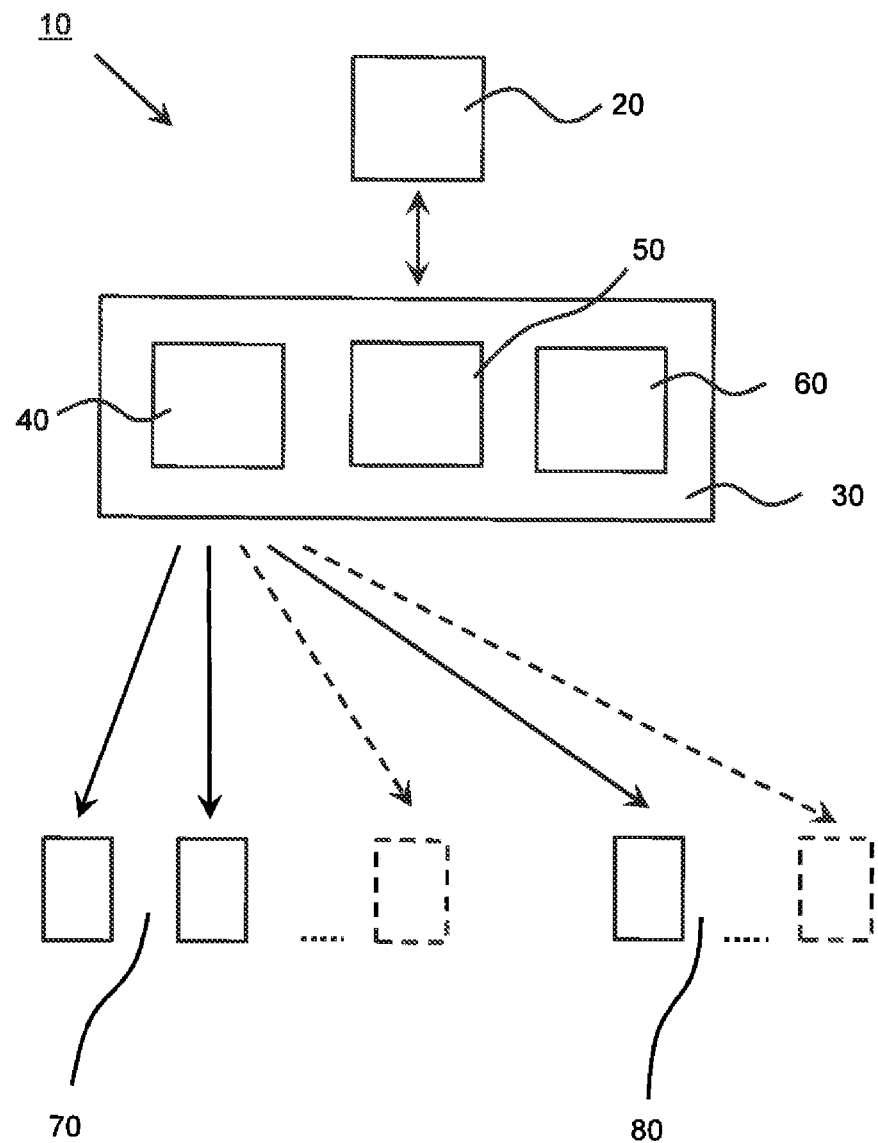

control device; determining a present value for the physiological parameter from the stream of monitoring data; and transmitting, in response to the present value exceeding the first threshold value, the signaling data from the control device to the first receiving device, and, in response to the present value exceeding the second threshold value, the signaling data from the control device to the second receiving device. Further, a medical device, a control device, and a computer program product are provided.

12 Claims, 2 Drawing Sheets

(51) Int. Cl.
*G08B 21/04* (2006.01)
*G16H 10/60* (2018.01)
*A61B 5/00* (2006.01)
*A61B 5/024* (2006.01)
*A61B 5/145* (2006.01)
*A61B 5/01* (2006.01)

(52) U.S. Cl.
CPC .......... *A61B 5/14532* (2013.01); *A61B 5/742* (2013.01); *A61B 5/7405* (2013.01); *G08B 21/0453* (2013.01); *G16H 10/60* (2018.01)

(58) Field of Classification Search
USPC .................................................. 340/870.09
See application file for complete search history.

METHOD FOR OPERATING A MEDICAL SYSTEM, COMPUTER PROGRAM PRODUCT, MEDICAL SYSTEM, AND CONTROL DEVICE

The present disclosure refers to a method for operating a medical system comprising a sensor device continuously monitoring a physiological parameter, computer program product, medical system, and control device.

BACKGROUND

In general, such methods and systems are used in order to determine characteristics of one or more physiological parameters for a patient. For example, glucose values may be sampled for the patient. The objective is to give the patient as well as the attending medical staff information which enables the patient to deal with his physiological parameter values in an improved and appropriate manner. The glucose level or some other physiological parameter may be determined by different measurement methods known as such. For example, the glucose level may be measured by means of an interstitial glucose sensor. Such sensor may be applied in a continuous measurement regime. Also, the glucose level may be determined by analyzing a capillary blood sample.

If it is determined, on the basis of the measured values, that the value sampled for the physiological parameter, e.g., glucose value, has exceeded a target range, medicine may be administered, for example by means of insulin injection or the oral administration of Metformin, an oral antidiabeticum. If the glucose values fall below the ideal or recommended level, sugar must be orally ingested, for example through food or drink. If the ideal level is exceeded for an extended period of time, there is the risk of serious health complications such as blindness, kidney damage, amputation of limbs or neuropathy. Very high short-term glucose levels can lead to nausea, dizziness, sweating or even conditions of confusion. Thus, it is particularly important for a patient with diabetes to know his glucose values at all times so that he is able to implement the appropriate measures to avoid the blood sugar values deviating from the target range.

Glucose values for a patient may be determined according to a continuous measurement regime. Such measurements are also known as CGM measurements (Continuous Glucose Monitoring). In this process, the glucose values are measured, e.g., every minute such that, for example, the progress of the glucose value can be collected over an entire day or longer. This allows the determination of short-term or medium-term trends in glucose progression and the identification of patterns of glucose variations over the day. It also allows to detect in realtime dangerous situations of a patient with diabetes (e.g. hypoglycaemia) and to warn or alarm the patient, respectively.

Document WO 2015/066051 A2 discloses a sensor system provided with an interactive interface. If the system receives inputs which indicate that the user's analyte level is below a threshold and is not acknowledging alarms, via the Internet of Things (TOT), a hierarchy of alarms can be transmitted. First, text messages are sent to pre-determined followers that are nearby according to a known GPS location. Followers may be notified based on their proximity to the person, e.g., there is no need to notify a person who is determined to be located in a different state. Followers include all members of a community of users. For example, a follower network of all DexCom users can be created whereby each user is identified as a follower of another person in the network who is nearby. The follower network may be configured based on privacy preferences or other reporting criteria. Caregivers can be arranged in groups which are notified in the night or during the day. Also, the information to be shared can be tailored.

SUMMARY

It is the object to provide improved technologies for operating a medical system having a sensor device for continuously monitoring a physiological parameter.

According to one aspect, a method for operating a medical system is provided. The medical system comprises a sensor device continuously monitoring a physiological parameter, a control device, and receiving devices, the method, in the control device. The method is comprising: providing a first threshold value for the physiological parameter in the control device, the first threshold value being assigned to a first receiving device configured to notify a user of the first receiving device in response to receiving signaling data from the control device; providing a second threshold value for the physiological parameter in the control device, the second threshold value being different from the first threshold value and assigned to a second receiving device which is different from the first receiving device and configured to notify a user of the second receiving device in response to receiving the signaling data from the control device; receiving a stream of monitoring data indicating a physiological parameter continuously monitored by the sensor device in the control device; and determining a present value for the physiological parameter from the stream of monitoring data. In response to the present value exceeding the first threshold value, the signaling data are transmitted from the control device to the first receiving device, and, in response to the present value exceeding the second threshold value, the signaling data are transmitted from the control device to the second receiving device.

According to another aspect, a medical system is provided, comprising a sensor device continuously monitoring a physiological parameter, a control device, and receiving devices. The medical system is configured for: providing a first threshold value for the physiological parameter in the control device, the first threshold value being assigned to a first receiving device configured to notify a user of the first receiving device in response to receiving signaling data from the control device; providing a second threshold value for the physiological parameter in the control device, the second threshold value being different from the first threshold value and assigned to a second receiving device which is different from the first receiving device and configured to notify a user of the second receiving device in response to receiving the signaling data from the control device; receiving a stream of monitoring data indicating a physiological parameter continuously monitored by the sensor device in the control device; and determining a present value for the physiological parameter from the stream of monitoring data. In response to the present value exceeding the first threshold value, the signaling data are transmitted from the control device to the first receiving device, and, in response to the present value exceeding the second threshold value, the signaling data are transmitted from the control device to the second receiving device.

According to still another aspect, a control device is provided, the control device comprising an input device, configured to receive measurement data form a sensor device continuously monitoring a physiological parameter, a processing device, and an output device, configured to transmit signaling data. Further, the processing device is configured to: provide a first threshold value for the physiological parameter, the first threshold value being assigned to a first receiving device configured to notify a user of the first receiving device in response to receiving the signaling data; provide a second threshold value for the physiological parameter, the second threshold value being different from the first threshold value and assigned to a second receiving device which is different from the first receiving device and configured to notify a user of the second receiving device in response to receiving the signaling data; via the input device, receiving a stream of monitoring data indicating a physiological parameter continuously monitored by the sensor device; and determine a present value for the physiological parameter from the stream of monitoring data. In response to the present value exceeding the first threshold value, the signaling data are transmitted from the control device to the first receiving device, and, in response to the present value exceeding the second threshold value, the signaling data are transmitted from the control device to the second receiving device.

Further, a computer program product is provided.

The physiological parameter may be indicative of an analyte value or level.

The technologies proposed provide for the opportunity to notify different groups of receiving devices assigned to one or more person, for example, to one or more physicians or caregivers, based on a prioritizing scheme. Depending on an use situation, with regard to the medical system different schemes of notification can be implemented. Notification is imitated in response to a present value of the physiological parameter "crossing" a threshold value. The threshold value may define in upper limit or a lower limit with regard to the physiological parameter.

The method may further comprise determining whether the present value is exceeding the first and/or second threshold values for a pre-defined time range, and transmitting the signaling data from the control device to at least one of the first receiving device and the second receiving device only, if it is determined that the present value is exceeding the first and/or second threshold value for the pre-defined time range. The pre-defined time range which may be set by a user input received in the control device may be different for the first and second threshold values. As an alternative the same time range may apply to the first and second threshold values. The signaling data are sent to the first receiving device if the present value is exceeding the first threshold values for the pre-defined time range. The signaling data are sent to the second receiving device if it is determined that the present value is exceeding the second threshold values for the pre-defined time range applied for the second threshold value.

To at least one of the first and second threshold values, a plurality of receiving devices may be assigned. First signaling data may be transmitted to the first or the second receiving device in response to the present value exceeding the threshold value. Further signaling data may be transmitted to the first or second receiving device after the present value has exceeded the threshold value for a time period equal to the pre-defined time range.

The method may further comprise providing device information for the plurality of receiving devices in the control device; prioritizing the receiving devices from the plurality of receiving devices according to the device information, thereby, determining a prioritized order of the receiving devices; and transmitting the signaling data from the control device to the one or all receiving devices from the plurality of receiving devices according to the prioritized order.

The device information, for example, may comprise information about an operation time of the receiving device and/or a geographical area of operation of the receiving device. Present device information for the plurality of receiving devices may be provided. The present device information may be compared to the device information available for the plurality of receiving devices. Based on such comparison, it may be determined to which receiving device of the prioritized order of devices signaling data are transmitted.

The method may further comprise providing parameter information defining a parameter prioritized order of the receiving devices; and transmitting the signaling data from the control device to the one or all receiving devices from the plurality of receiving devices according to the parameter prioritized order. For example, the parameter information may indicate a present physiological parameter selected from a group of physiological parameters. The selected physiological parameter may be assigned to a group of receiving devices. This information may be analyzed in the process of determining to which receiving device(s) signaling data is transmitted. Depending on the physiological parameter at present continuously monitored different groups of receiving devices may be selected.

Further, present value information with the signaling data may be provided, the present value information indicating the present value of the physiological parameter. In this embodiment, in addition to the notification regarding the present value exceeding the threshold value, the present value itself is transmitted.

Additional information with the signaling data may be provided, the additional information being selected from the following group: location information, and clinical information for a patient. Location information may be provided by geographical coordinates, for example, GPS coordinates.

The transmitting of the signaling data may comprise calling a communication device of the user. The receiving device itself may be provided as a mobile phone, a paging device or a tablet computer. As an alternative, the receiving device, in response to receiving the signaling data, may initiate calling the communication device which may be provided as a telephone, a mobile phone or some other device available for exchanging at least audio messages.

The sensor device may continuously monitor a physiological parameter from the following group: glucose level, heart rate, and body temperature. The threshold values may relate to the glucose level, e.g., a hypo limit which the patient fell below for a time span, e.g., longer than 10 to 30 min.

The method, in the first receiving device and/or the second receiving device may further comprise receiving the signaling data, and notifying the user by outputting, via an output device, at least one of video data and audio data. While video data may be outputted via display, audio data may be outputted by means of a speaker of the receiving device.

The method may further comprise, within the prioritized order, assigning a priority of order to a receiving device from the plurality of receiving devices; receiving availability information in the control device, the availability information indicating amended availability for the receiving device; and within the prioritized order, assigning an amended priority of order to the receiving device in response to the receiving the availability information in the control device.

For example, the availability information may indicate that the receiving device will not be available for receiving the signaling data for notification for a time period, e.g., some hours or a full day. Such information may indicate that the person to whom the receiving device is assigned will not be available for responding to the notification. In response to the availability information, the receiving device may be assigned a lower priority within the prioritized order of the receiving devices. Even a "zero priority" may be assigned indicating non-availability, for example, for a limited time period. As an alternative, the receiving device for which the availability information is received in the control device may be assigned from a group of receiving devices of low priority to a group of receiving devices with high(er) priority. The low and the high priority may be assigned to different threshold values.

The method may further comprise receiving response information in the control device, the response information indicating a user response from a receiving device notified by receiving the signaling data; and interrupting further transmission of the signaling data, thereby, preventing transmission of the signaling data to at least one remaining receiving device from the plurality of receiving devices within the prioritized order. The at least one remaining device has not received the signaling data before. The user response may indicate that the user of the receiving device which had received the signaling data, e.g. an alarming signal, and from which, after receiving a user input, the response information is submitted to the control device will act in response to receiving the signaling data. For example, the caregiver or physician will take care of the patient. The response information may comprise at least one of a text message and a control signal. In response to receiving the response information in the control device, further transmission is prevented to receiving devices having assigned the same priority like receiving device from which the response information is received and/or a lower priority within the prioritized order.

In response to receiving the response information in the control device, a follow-up information or follow-up signaling data may be generated in the control device and transmitted to one or more receiving devices having, within the prioritized order, assigned the same or a lower priority (device priority) compared to the receiving device from which the response information was sent to the control device. The follow-up information may be transmitted to any receiving device which has been notified before. The follow-up information may be indicating by at least one of a text message and an action signal that at least one of the receiving devices has responded to receiving the signaling data.

The alternatives outlined above may apply to the medical system as well as the control device.

The control device may be provided in an integrated system comprising, in addition, the sensor device. As an alternative, the control device may be provided separately from the sensor device, wherein data exchange between the control device and the sensor device may comprise exchanging data over at least one of a wired and a wireless communication line.

With regard to a glucose measurement or monitoring, a glucose level or value may be determined by analyzing a blood sample via e.g. spot monitoring, and, as an alternative or in addition, by continuous glucose monitoring (CGM) via a fully or partially implanted sensor. In general, in the context of CGM an analyte value or level indicative of a glucose value or level in the blood may be determined. The analyte value may be measured in an interstitial fluid.

The measurement may be performed subcutaneously or in vivo (in contrast to transdermal or in vitro). CGM may be implemented as a nearly real-time or quasi-continuous monitoring procedure frequently or automatically providing/updating analyte values without user interaction.

DESCRIPTION OF FURTHER EMBODIMENTS

Following, embodiments, by way of example, are described with reference to figures. In the figures show:

FIG. 1 a schematic representation of a medical system, and

Figure 2:
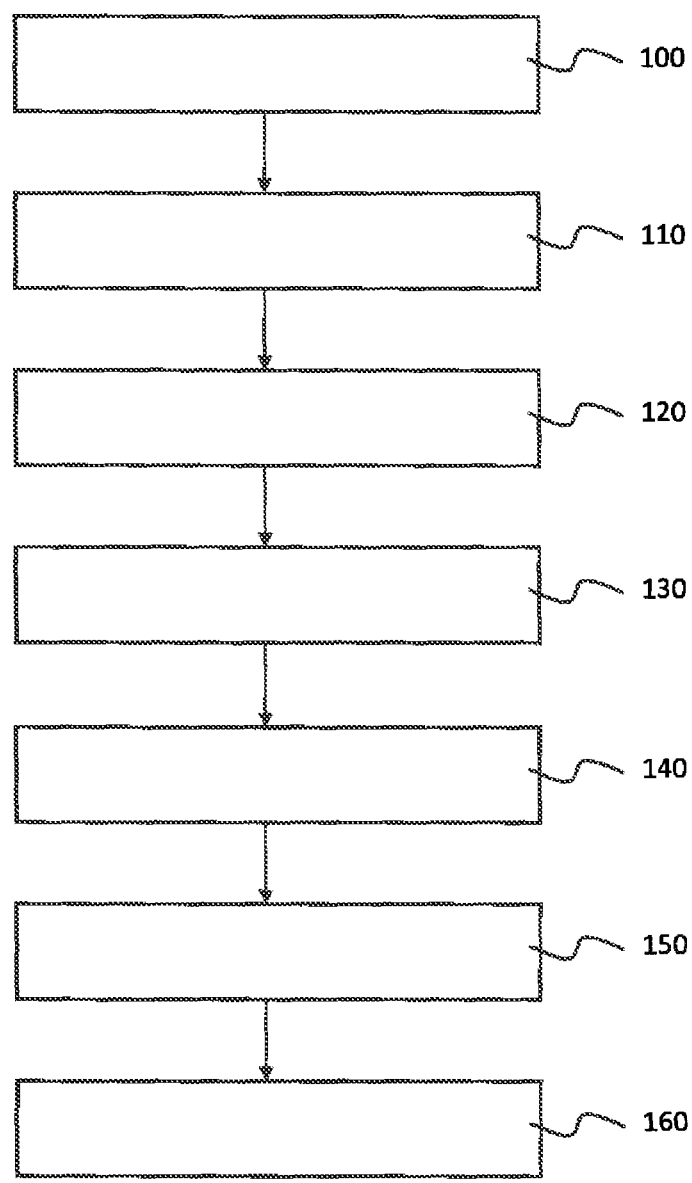

FIG. 2 a schematic representation with regard to a method for operating the medical system.

Referring now to FIG. 1, a schematic representation of a medical system 10 is shown. The medical system 10 is provided with a sensor device 20 configured to continuously monitor or sample a physiological parameter for a patient. For example, the sensor device 20 may comprise a continuous glucose monitor (CGM). The CGM may use a subcutaneous sensor to sense and monitor the amount of glucose in the subcutaneous fluid of the patient. As an alternative, the sensor device 20 may be continuously monitoring a heart rate or a body temperature.

The readings detected by the sensor device 20 are communicated to a control or managing device 30. Communication between the various devices in the medical system 10 can be performed using wireless interfaces (e.g., Bluetooth) and/or wireline interfaces (e.g., USB). Communication protocols used can include, for example, protocols compliant with the IEEE 11073 standard as extended using guidelines provided by Continua® Health Alliance Design Guidelines.

The control device 30 comprises an input device 40, a processing device 50, and an output device 60. The input device 40 connected to the processing device 50 is configured to receive a stream of monitoring data indicating the physiological parameter continuously monitored by the sensor device 20 in the control device 30.

The stream of monitoring data is processed by the processing device 50. Specifically, by the processing device 50 it is determined whether a value of the physiological parameter, e.g., a present value, is exceeding a threshold value of the physiological parameter. Depending on the result of such determination signaling data is transmitted from the control device 30 via the output device 60. The signaling data is received by at least one of a first group 70 of receiving devices and a second group 80 of receiving devices. The receiving devices may also be referred to as caregiver devices. Each of the receiving devices is assigned to a user, specifically a caregiver. For example, the caregiver may be a healthcare professional. The receiving devices may be one of a mobile phone, a personal digital assistant (PDA), and a paging device. In general, the receiving devices may be provided as separated mobile devices. In case of continuously monitoring the glucose level of the patient, one or more of the receiving devices may be provided as a diabetes managing device comprising a software implementation of a diabetes manager.

In response to receiving the signaling data, the receiving devices of the first and the second group 70, 80 may output video data and/or audio data for notifying the respective user.

Referring to FIG. 2, a method for operating the medical system 10 is described. In step 100 a stream of monitoring data is received in the control device 30 via the input device 40. The stream of monitoring data is indicating the one or more physiological parameters continuously monitored by the sensor device 20. According to step 110, a present value for the physiological parameter(s) is determined by processing the stream of monitoring data by the processing device 50.

A first threshold value for the physiological parameter is provided in the control device 30 in step 120. Electronic information with regard to the first threshold value may be received in the processing device 50 from a memory device (not shown) provided in the control device 30 itself. As an alternative, the electronic information with regard to the first threshold value may be received from a central server station (not shown) of the medical system 10. The first threshold value is assigned to the first group 70 of receiving devices. According to such assignment, signaling data is sent to the first group 70 of receiving devices if the present value determined by the processing device 50 in the control device 30 is exceeding the first threshold value.

According to step 130, in the control device 30 a second threshold value for the physiological parameter is provided. The second threshold value is different from the first threshold value and is assigned to the second group 80 of receiving devices. With regard to the second threshold value, the aspects described for the first threshold value above may also apply.

In step 140, by the processing device 50 it is determined whether the present value for the physiological parameter is exceeding the first or the second threshold value. Depending on the result of such determination, in step 150, the signaling data is transmitted from the control device 30 via the output device 60 to the first and 7 or the second group 70, 80 of receiving devices. Thereby, depending on whether the first or the second threshold value is exceeded by the present value, a selected group of receiving devices is notified by the signaling data. The first and second threshold values may indicate different levels of critical conditions for the patient. With regard to the first and the second group 70, 80 of receiving devices, a prioritized order is defined in the control device 30.

A sub-prioritization may apply within the groups of receiving devices. For example, within a group of receiving devices the receiving device located closest to the control device 30 may be selected for receiving the signaling data. For such purpose, the control device 30 may receive location data indicating a present location (e.g., a global positioning system (GPS) location) for each of the receiving devices. The control device 30 may determine the receiving device located closest to the control device 30. As an alternative, in the control device 30 information may be provided indicating a fixed geographic position of the receiving devices of a group of receiving devices. In response to determining a present value exceeding one of the threshold values, the control device 30 may determine the receiving device closest to the position of the control device 30 from the group of receiving devices assigned to the threshold value exceeded by the present value.

The first and the second group 70, 80 of receiving devices may comprise one or more receiving devices assigned to both groups. However, there is at least one receiving device which is either only a member of the first group 70 or the second group 80.

According to an aspect of the present disclosure, prioritizing the caregiver group may be based on measured physiological parameters, e.g., glucose value. Such prioritization allows for simplifying notification of caregivers/followers. For example, if the patient is in a high or low glucose condition, caregivers in the group with the highest priority may be notified, after the glucose level exceeds a specific first threshold value. If none of them is responding appropriately and the second threshold value is exceeded, the available caregivers in the group with the next higher priority get notified. This allows for a simplified and more reliable notification system, which allows notifying specific caregivers or followers depending on severity of condition.

With regard to the groups 70, 80 of receiving devices, the parameters defining priority may include further factors. One example is to additionally include the location, e.g., from GPS. In that example based on the priority resulting from, e.g., the glucose level the closest caregiver of that priority group may be notified. Furthermore, the status of caregiver may be taken into account. In that example, based on the priority resulting from, e.g., the glucose level, the caregiver of that priority group who is available may be notified.

The signaling data transmitted to the receiving device assigned to the follower or caregiver can include at least one of the glucose value, the time span of the condition, the location of the patient, and additional clinical information of the patient. In addition or as an alternative, an action may be triggered, e.g. call caregiver or emergency call.

Furthermore, a return or response message may be triggered and may include the status of the caregiver or a message is sent to the group of receiving devices, the message indicating that the situation will be taken care of. If certain time passes without reaction, the receiving device assigned to a caregiver may be set to be not available and the control device 30 will select the next appropriate caregiver for notification.

The invention claimed is:

1. A method for operating, a medical system comprising a sensor device continuously monitoring a physiological parameter, a control device, and receiving devices, the method, in the control device, comprising:
    providing a first threshold value for the physiological parameter in the control device, the first threshold value being assigned to a first receiving device configured to notify a user of the first receiving device in response to receiving signaling data from the control device;
    providing a second threshold value for the physiological parameter in the control device, the second threshold value being different from the first threshold value and assigned to a second receiving device which is different from the first receiving device and configured to notify a user of the second receiving device in response to receiving the signaling data from the control device;
    receiving a stream of monitoring data indicating a physiological parameter continuously monitored by the sensor device in the control device;
    determining a present value for the physiological parameter from the stream of monitoring data; and
    transmitting,
        in response to the present value exceeding the first threshold value, the signaling data from the control device to the first receiving device, and
        in response to the present value exceeding the second threshold value, the signaling data from the control device to the second receiving device,
    wherein to at least one of the first and second threshold values a plurality of receiving devices is assigned and the method further comprises:
        providing device information for the plurality of receiving devices in the control device;

prioritizing the receiving devices from the plurality of receiving devices according to the device information, thereby, determining a prioritized order of the receiving devices;

transmitting the signaling data from the control device to the one or all receiving devices from the plurality of receiving devices according to the prioritized order;

receiving response information in the control device, the response information indicating a user response from a receiving device notified by receiving the signaling data; and interrupting further transmission of the signaling data, thereby, preventing transmission of the signaling data to at least one remaining receiving device from the plurality of receiving devices within the prioritized order.

2. Method according to claim 1, further comprising determining whether the present value is exceeding the first and/or second threshold values for a predefined time range, and transmitting the signaling data from the control device to at least one of the first receiving device and the second receiving device only, if it is determined that the present value is exceeding the first and/or second threshold value for the pre-defined time range.

3. Method according to claim 1, further comprising:
providing parameter information defining a parameter prioritized order of the receiving devices; and
transmitting the signaling data from the control device to the one or all receiving devices from the plurality of receiving devices according to the parameter prioritized order.

4. Method according to claim 1, further comprising providing present value information with the signaling data, the present value information indicating the present value of the physiological parameter.

5. Method according to claim 1, further comprising providing additional information with the signaling data, the additional information being selected from the following group: location information, and clinical information for a patient.

6. Method according to claim 1, wherein the transmitting the signaling data comprises calling a communication device of the user.

7. Method according to claim 1, wherein the sensor device is continuously monitoring a physiological parameter from the following group: blood glucose level, heart rate, and body temperature.

8. Method according to claim 1, in the first receiving device and the second receiving device, respectively, further comprising:
receiving the signaling data; and
notifying the user by outputting, via an output device, at least one of video data and audio data.

9. Method according to claim 1, further comprising:
within the prioritized order, assigning a priority of order to a receiving device from the plurality of receiving devices within the prioritized order;
receiving availability information in the control device, the availability information indicating amended availability for the receiving device; and
within the prioritized order, assigning an amended priority of order to the receiving device in response to the receiving the availability information in the control device.

10. Computer program product, preferably stored on a storage medium and configured to perform the method according to claim 1 during operation on a data processing device.

11. A medical system, comprising
a sensor device continuously monitoring a physiological parameter;
a control device; and
receiving devices;
the medical system being configured for
providing a first threshold value for the physiological parameter in the control device, the first threshold value being assigned to a first receiving device configured to notify an user of the first receiving device in response to receiving signaling data from the control device,
providing a second threshold value for the physiological parameter in the control device, the second threshold value being different from the first threshold value and assigned to a second receiving device which is different from the first receiving device and configured to notify a user of the second receiving device in response to receiving the signaling data from the control device;
receiving a stream of monitoring data indicating a physiological parameter continuously monitored by the sensor device in the control device;
determining a present value for the physiological parameter from the stream of monitoring data; and
transmitting,
in response to the present value exceeding the first threshold value, the signaling data from the control device to the first receiving device, and
in response to the present value exceeding the second threshold value, the signaling data from the control device to the second receiving device
wherein to at least one of the first and second threshold values a plurality of receiving devices is assigned and the medical system is further configured for:
providing device information for the plurality of receiving devices in the control device;
prioritizing the receiving devices from the plurality of receiving devices according to the device information, thereby, determining a prioritized order of the receiving devices;
transmitting the signaling data from the control device to the one or all receiving de-vices from the plurality of receiving devices according to the prioritized order;
receiving response information in the control device, the response information indicating a user response from a receiving device notified by receiving the signaling data; and
interrupting further transmission of the signaling data, thereby, preventing transmission of the signaling data to at least one remaining receiving device from the plurality of receiving devices within the prioritized order.

12. A control device, comprising
an input device, configured to receive measurement data form a sensor device continuously monitoring a physiological parameter;
a processing device; and
an output device, configured to transmit, signaling data;
the processing device being configured to:
provide a first threshold value for the physiological parameter, the first threshold value being assigned to a first receiving device configured to notify a user of the first receiving device in response to receiving the signaling data;
provide a second threshold value for the physiological parameter, the second threshold value being different from the first threshold value and assigned to a second receiving device which is different from the first receiving device and configured to notify an user of the second receiving device in response to receiving the signaling data;
via the input device, receiving a stream of monitoring data indicating a physiological parameter continuously monitored by the sensor device;
determine a present value for the physiological parameter from the stream of monitoring data; and
transmitting,
- in response to the present value exceeding, the first threshold value, the signaling data from the control device to the first receiving device, and
- in response to the present value exceeding the second threshold value, the signaling data from the control device to the second receiving device wherein to at least one of the first and second threshold values a plurality of receiving devices is assigned, device information for the plurality of receiving devices is provided in the control device, and the control device is further configured for:
prioritizing the receiving devices from the plurality of receiving devices according to the device information, thereby, determining a prioritized order of the receiving devices;
transmitting the signaling data to the one or all receiving de-vices from the plurality of receiving devices according to the prioritized order;
receiving response information, the response information indicating a user response from a receiving device notified by receiving the signaling data; and
interrupting further transmission of the signaling data, thereby, preventing transmission of the signaling data to at least one remaining receiving device from the plurality of receiving devices within the prioritized order.

\* \* \* \* \*